US011864876B2

(12) United States Patent
Lin et al.

(10) Patent No.: US 11,864,876 B2
(45) Date of Patent: Jan. 9, 2024

(54) LIGHT-TO-DIGITAL CONVERTER

(71) Applicants: IMEC VZW, Leuven (BE); Katholieke Universiteit Leuven, Leuven (BE); Stichting IMEC Nederland

(72) Inventors: Qiuyang Lin, Eindhoven (NL); Jiawei Xu, Eindhoven (NL); Shuang Song, Eindhoven (NL); Nick Van Helleputte, Korbeek-Dijle (BE); Filip Tavernier, Leuven (BE)

(73) Assignees: IMEC VZW, Leuven (BE); KATHOLIEKE UNIVERSITEIT LEUVEN KU LEUVEN, Leuven (BE); STICHTING IMEC NEDERLAND, AE Eindhoven (NL)

( * ) Notice: Subject to any disclaimer, the term of this patent is extended or adjusted under 35 U.S.C. 154(b) by 473 days.

(21) Appl. No.: 16/886,714

(22) Filed: May 28, 2020

(65) Prior Publication Data
US 2020/0375484 A1 Dec. 3, 2020

(30) Foreign Application Priority Data

May 29, 2019 (EP) .................................... 19177264

(51) Int. Cl.
*A61B 5/024* (2006.01)
*A61B 5/00* (2006.01)
*G01J 1/44* (2006.01)
(52) U.S. Cl.
CPC ........ *A61B 5/02427* (2013.01); *A61B 5/0042* (2013.01); *A61B 5/0075* (2013.01);
(Continued)
(58) Field of Classification Search
CPC . A61B 5/02427; A61B 5/0042; A61B 5/0075; A61B 5/6826; G01J 1/44; G01J 2001/446
See application file for complete search history.

(56) References Cited

U.S. PATENT DOCUMENTS

2016/0025777 A1* 1/2016 Deliwala ................ G01R 19/25
324/115
2017/0055860 A1 3/2017 Vermeulen et al.
2019/0313954 A1* 10/2019 Yoo ..................... H01L 23/5387

FOREIGN PATENT DOCUMENTS

| CN | 204346585 U | | 5/2015 | |
| CN | 207369179 U | * | 5/2018 | .......... H03M 1/1205 |
| EP | 3406194 A1 | | 11/2018 | |

OTHER PUBLICATIONS

Kestert et al., "ADC Architectures VIII: Integrating ADCs", MT-027 Tutorial, Analog Devices, 2009.
(Continued)

*Primary Examiner* — Rochelle D Turchen
(74) *Attorney, Agent, or Firm* — Moser Taboada

(57) ABSTRACT

A light-to-digital converter (2) comprises a light-to-current converter (10); a current integrator (4) with an integrator output (30) resettable to a baseline level; and a counter (18) with a digital output (26), wherein the light-to-current converter (10) is switchably connectable as a positive integration input to the current integrator (4), for, during a light-collecting phase (404-406), integrating a current from the light-to-current converter (10), the integrator output (30) starting from the baseline value and ending at a value to be digitized; a reference current source (14) is switchably connectable as a negative integration input to the current integrator (4), for, during a counting phase (406-408) subsequent to the light-collecting phase (404-406), integrating a reference current from the reference current source (14), the integrator output (30) starting from the value to be digitized and ending at the baseline value, the time spent integrating the reference current corresponding to the value to be digitized; and the counter (18) is configured for measuring the time.

12 Claims, 6 Drawing Sheets

(52) U.S. Cl.
CPC .............. *A61B 5/6826* (2013.01); *G01J 1/44* (2013.01); *G01J 2001/446* (2013.01)

(56) References Cited

OTHER PUBLICATIONS

Schönle et al. "A power-efficient multi-channel PPG ASIC with 112dB receiver DR for pulse oximetry and NIRS," 2017 IEEE Custom Integrated Circuits Conference (CICC), Austin, TX, 2017, pp. 1-4.
Extended European Search Report in EP19177264.9, dated Dec. 2, 2019.

* cited by examiner

LIGHT-TO-DIGITAL CONVERTER

CROSS-REFERENCE TO RELATED APPLICATIONS

This application claims priority to European Patent Application No. 19177264.9, filed on May 29, 2019, which is hereby incorporated by reference in its entirety.

TECHNICAL FIELD

The present inventive concept relates to a light-to-digital converter, to a photoplethysmogram (PPG) system, to a functional near-infrared spectroscopy (fNIRS) system, and to a method of light-to-digital conversion.

BACKGROUND

Light-to-digital converters may for example be used in photoplethysmogram (PPG) systems or in functional near-infrared spectroscopy (fNIRS) systems.

Such optical sensing systems on the human body providing timely information on health status to layperson as well as to medical practitioners. They provide higher user comfort than other methods such as electrocardiography (ECG), since, in contrast to the latter, wet electrodes and skin preparation are not required.

PPG is a common optical sensing technique, measuring heart rate and peripheral oxygen saturation (SpO2). The PPG signal contains a DC component from bones, muscles, etc., and an AC component from the heart activity. The AC/DC ratio can be as low as 0.05%, putting a high requirement on the dynamic range (DR) of the light-to-digital converter (typically >80 dB).

fNIRS can be used for brain monitoring, for example together with EEG monitoring. Typically, wavelengths in the range 650 nm to 950 nm are used. A light source and a light detector, such as an LED-and-photodiode pair, are deployed on the head with a distance of at least several centimeters, allowing light which penetrates deep into the brain and scatters to be captured. Due to the long light path through the head, a high dynamic range (typically >100 dB) is required.

SUMMARY

An objective of the present inventive concept is to provide a low-power light-to-digital converter that still provides a high dynamic range.

To this end, according to a first aspect, there is provided a light-to-digital converter, comprising a light-to-current converter; a current integrator with an integrator output resettable to a baseline level; and a counter with a digital output, wherein the light-to-current converter is switchably connectable as a positive integration input to the current integrator, for, during a light-collecting phase, integrating a current from the light-to-current converter, the integrator output starting from the baseline value and ending at a value to be digitized; a reference current source is switchably connectable as a negative integration input to the current integrator, for, during a counting phase subsequent to the light-collecting phase, integrating a reference current from the reference current source, the integrator output starting from the value to be digitized and ending at the baseline value, the time spent integrating the reference current corresponding to the value to be digitized; and the counter is configured for measuring the said time.

In this way, the integrator is used both as a signal readout frontend and for analog-to-digital conversion. This simplifies the system architecture, reducing the number of required components, which lowers the power requirements, while still allowing for a high dynamic range. In particular, compared to systems using a separate readout frontend and a high-resolution analog-to-digital converter (ADC), a considerable power saving is achieved, the integrator providing transimpedance amplification, noise anti-aliasing, signal sampling and digitalizing in one component, instead of using separate components.

According to an embodiment, the light-to-digital converter further comprises a comparator configured to compare the integrator output with a reference level corresponding to the baseline level, wherein an output of the comparator is connected to the counter.

This allows for an accurate yet simple way of determining when the counter should stop.

According to an embodiment, the light-to-digital converter further comprises the reference current source.

According to an embodiment the reference current is a constant current.

This provides a direct proportional relationship between the time measured by the counter and the integrated current, allowing for a measurement with high accuracy.

According to an embodiment the light-to-current converter comprises a photodiode.

Photodiodes are cheap, while still providing good sensitivity.

Alternatively, according to an embodiment, the light-to-current converter comprises a photomultiplier.

Photomultiplier provide excellent sensitivity to light.

According to an embodiment, the integrator is a single-ended integrator with a capacitor as a feedback component.

This provides a simple, yet accurate, circuitry for the integrator.

According to an embodiment, the integrator is a differential integrator with a pair of capacitors as feedback components.

As compared to a single-ended integrator, this allows for a doubled dynamic range, a better common mode rejection ratio, a better power supply rejection ratio, and eased comparator kick-back effect at the expense of higher complexity and thereby higher power requirements.

According to an embodiment, the integrator is based on current-sensing circuitry.

This provides good stability and fast settling of the integrator, at the expense of higher power requirements. In particular, this decouples the light-to-digital converter from the integrator, which is useful, for example, if the light-to-digital converter has a large parasitic capacitance or limited driving ability.

According to an embodiment, the light-to-digital converter further comprises a control unit controlling the counter and switching of the light-to-current converter and of the reference current source.

According to a second aspect, there is provided a photoplethysmogram, PPG, system comprising the light-to-digital converter of the first aspect.

This is a particularly favorable application of the light-to-digital converter.

Advantages and embodiments of this second aspect are at least the same as and/or compatible with those described above in conjunction with the first aspect.

According to a third aspect, there is provided a functional near-infrared spectroscopy, fNIRS, system comprising the light-to-digital converter of the first aspect.

This is another particularly favorable application of the light-to-digital converter.

Advantages and embodiments of this third aspect are at least the same as and/or compatible with those described above in conjunction with the first aspect.

According to a fourth aspect, there is provided a method of light-to-digital conversion, comprising during a light-collecting phase, a current integrator, having an integrator output, integrating a current from a light-to-current converter connected as a positive integration input, the integrator output starting from the baseline value and ending at a value to be digitized; and, thereafter; in a counting phase, the current integrator integrating a reference current connected as a negative integration input, the integrator output starting from the value to be digitized and ending at the baseline value, the time spent integrating the reference current corresponding to the value to be digitized, wherein a counter, providing a digital output, measures the said time.

Advantages and embodiments of this fourth aspect are at least the same as and/or compatible with those described above in conjunction with the first aspect.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1A:
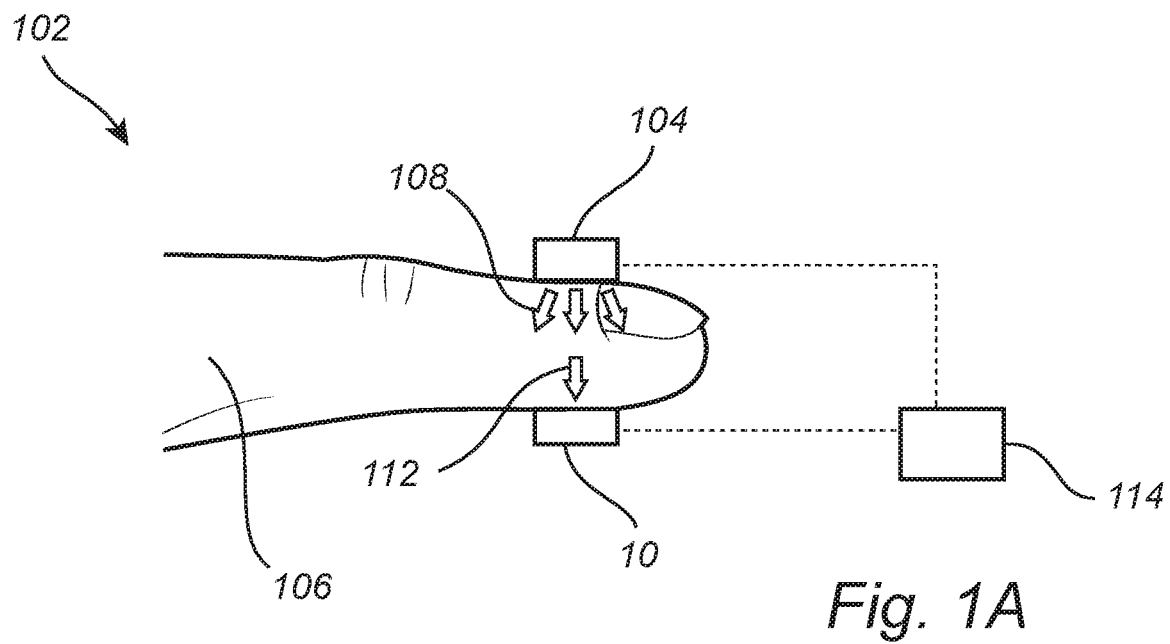
FIG. 1A schematically shows a photoplethysmogram (PPG) system.

FIG. 1A illustrates schematically a photoplethysmogram (PPG) system 102.

An LED 104 shines light into a finger 106 of a patient, as indicated by three arrows 108. The light is scattered and absorbed by the bones, muscle, blood, etc., of the finger 106. Some of the light reaches a photodiode (PD) 10, which is connected to a readout and control system 114, which also controls the LED 104. A typical distance between the LED 104 and the photodiode 110 is less than 1 cm.

Figure 1B:
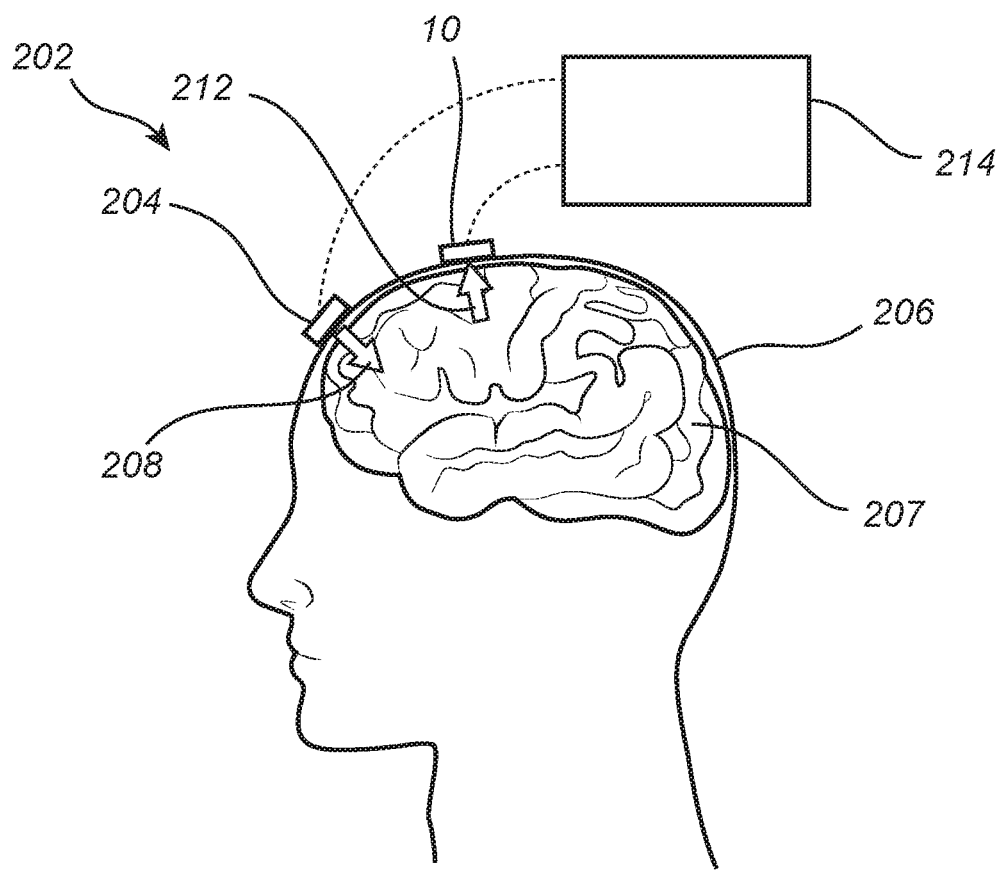
FIG. 1B schematically shows a functional near-infrared spectroscopy (fNIRS) system.

FIG. 1B illustrates schematically a functional near-infrared spectroscopy (fNIRS) system 202. An LED 204 shines light into the head 106 of a patient. The light penetrates deep into the brain 107, where it is scattered. Some of the light reaches a photodiode (PD) 10, which is connected to a readout and control system 214, which also controls the LED 204. A typical distance between the LED 104 and the photodiode 110 is less than 3 cm. Typically, there are several LEDs 204 (not shown) emitting light of different wavelengths.

Figure 2:
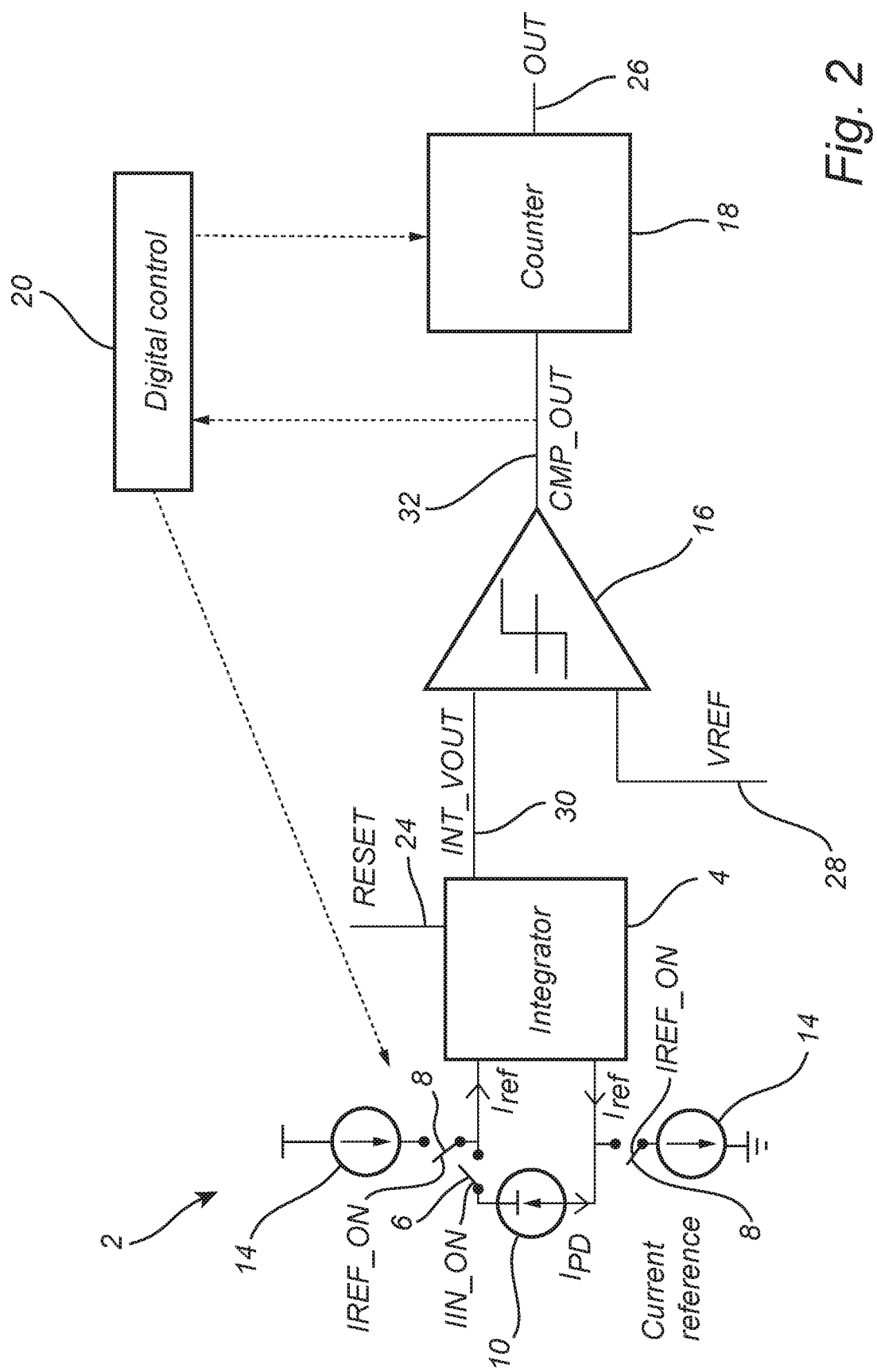
FIG. 2 shows a light-to-digital converter at block level.

FIG. 2 schematically shows a light-to-digital converter 2 at block level. The light-to-digital converter 2 may be comprised in the readout and control system 114 and photodiode 10 of the PPG system 102 of FIG. 1a, or in the readout and control system 214 and photodiode 10 of the fNIRS system 202 of FIG. 1b.

A photodiode 10 functions as a light-to-digital converter. Alternatively (not shown), the light-to-digital converter may comprise a photomultiplier tube. The photodiode 10 is connected to a current integrator 4, through a switch 6 controlled by a control line IIN_ON.

The charge collected by the light-to-digital converter during a certain time interval corresponds to the amount of light collected during that time interval. The integral of the current $I_{PD}$ produced by the light-to-current converter 10 during that time interval corresponds to the collected charge. Therefore, integrating the current from the light-to-current converter 10 during that time interval gives a measure of the light collected.

The integrator output 30 INT_VOUT of the integrator 4 is resettable to a baseline, reference, level VREF, corresponding to zero integrated current, through a reset line 24 RESET. The photodiode 10 is connected to the integrator 4 such that the current $I_{PD}$ constitutes a positive integration input to the integrator 4, i.e., the integrated value at the integrator output 30 INT_VOUT increases as the current $I_{PD}$ flows through the integrator 4.

Further, the light-to-digital converter 2 comprises one (not shown) or two (shown) reference current sources 14, connected to the current integrator through one or two switches 8 and controlled by a control line IREF_ON.

The reference current source 14 is—or the reference current sources 14 are—configured to generate a reference current $I_{ref}$, which typically is a constant current.

The reference current source 14 is—or the reference current sources 14—are connected to the current integrator 4 in such a way that the reference current $I_{ref}$ constitutes a negative integration input to the integrator 4, i.e., the integrated value at the integrator output 30 decreases as the current $I_{ref}$ flows through the integrator 4.

The light-to digital converter may comprise a means for determining when the integrator output corresponds to the baseline value, for stopping the counter 18 (see below). This may be achieved through a comparator configured to compare the integrator output with a reference level corresponding to the baseline level, wherein an output of the comparator is connected to the counter, or by any other suitable means. In the light-to-digital converter depicted in FIG. 2, the integrator output INT_VOUT 30 of the integrator 4 is connected to a comparator 16 comparing the integrator output INT_VOUT 30 of the integrator 4 with the reference level VREF 28. Alternatively (not shown in FIG. 2, but cf. FIGS. 3B and 3B), the integrator may have a differential output so that the reference level corresponds to a zero difference between the two output lines of the differential output. The output 32 of the comparator 16 is connected to the counter 18.

A counter 18 is configured to measure the length of a time interval and has a digital output OUT 26, which is the output of the light-to-digital converter 2. The output OUT 26 of the counter 18 may be serial or parallel, comprising one or more bits.

The light-to-digital converter 2 may comprise a digital control unit 20 controlling the switch control lines IIN_ON for the switch 6 and IREF_ON for the switch(es) 8 and monitors the output CMP_OUT 32 of the comparator 16, as indicated by dashed lines. The counter 18 is as well controlled by the digital control unit 20. Thus, the light-to-digital converter 2 may comprise a control unit 20 controlling the counter 18 and switching 6 of the light-to-current converter and switching 8 of the one or two reference current sources 14.

In the following, with reference to FIGS. 3A, 3B, and 3C, three specific examples of light-to-digital converters 2 will be described. They are all encompassed by the block-level description above in conjunction with FIG. 2. Specifics beyond what was described there will be discussed, while shared common features discussed above will not be repeated.

Figure 3A:
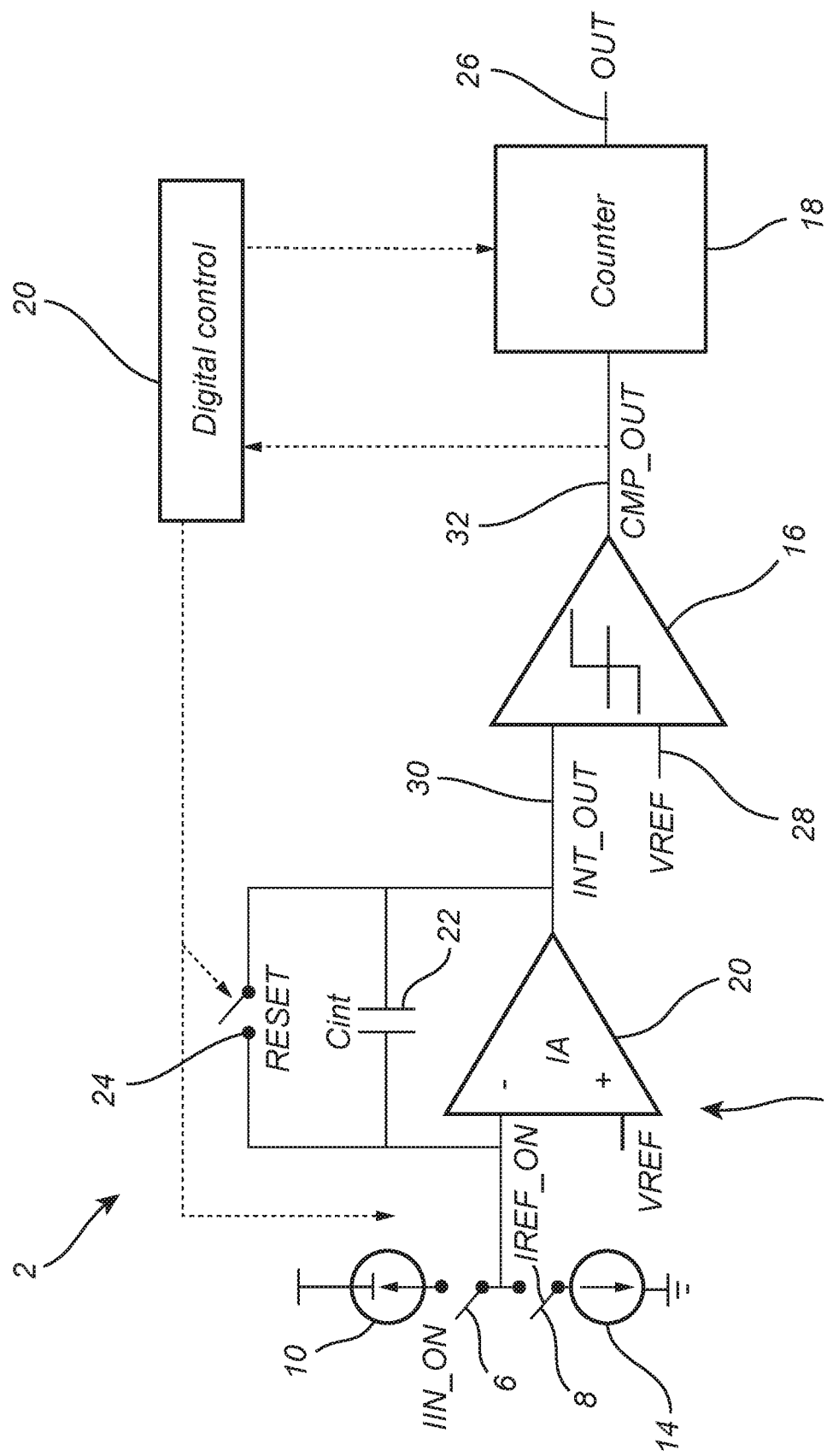
FIG. 3A shows a light-to-digital converter with a single-ended integrator with a capacitor as a feedback component.

FIG. 3A shows an example light-to-digital converter 2. Here, the integrator 4 comprises an integrator amplifier 20 and a capacitor $C_{int}$ 22. The integrator amplifier 20 has a positive input, a negative input, and an output 30, which is the output INT_VOUT 30 of the integrator 4. The capacitor 22 is connected between the output 30 of the integrator amplifier 20 and the negative input of the integrator amplifier 20. The light-to-current converter, in the form of a photodiode 10, and the reference current source 14, are connected to the negative input of the integrator amplifier 20 through respective switches 6 and 8. Thus, the integrator 4 is a single-ended integrator 4 with a capacitor 22 as a feedback component. The reference level VREF is provided to the positive input of the integrator amplifier 4. The integrator 4 may be reset by closing a reset switch 24 connected in parallel to the capacitor 22 and controlled by the digital control unit 20 though a reset line RESET.

Figure 3B:
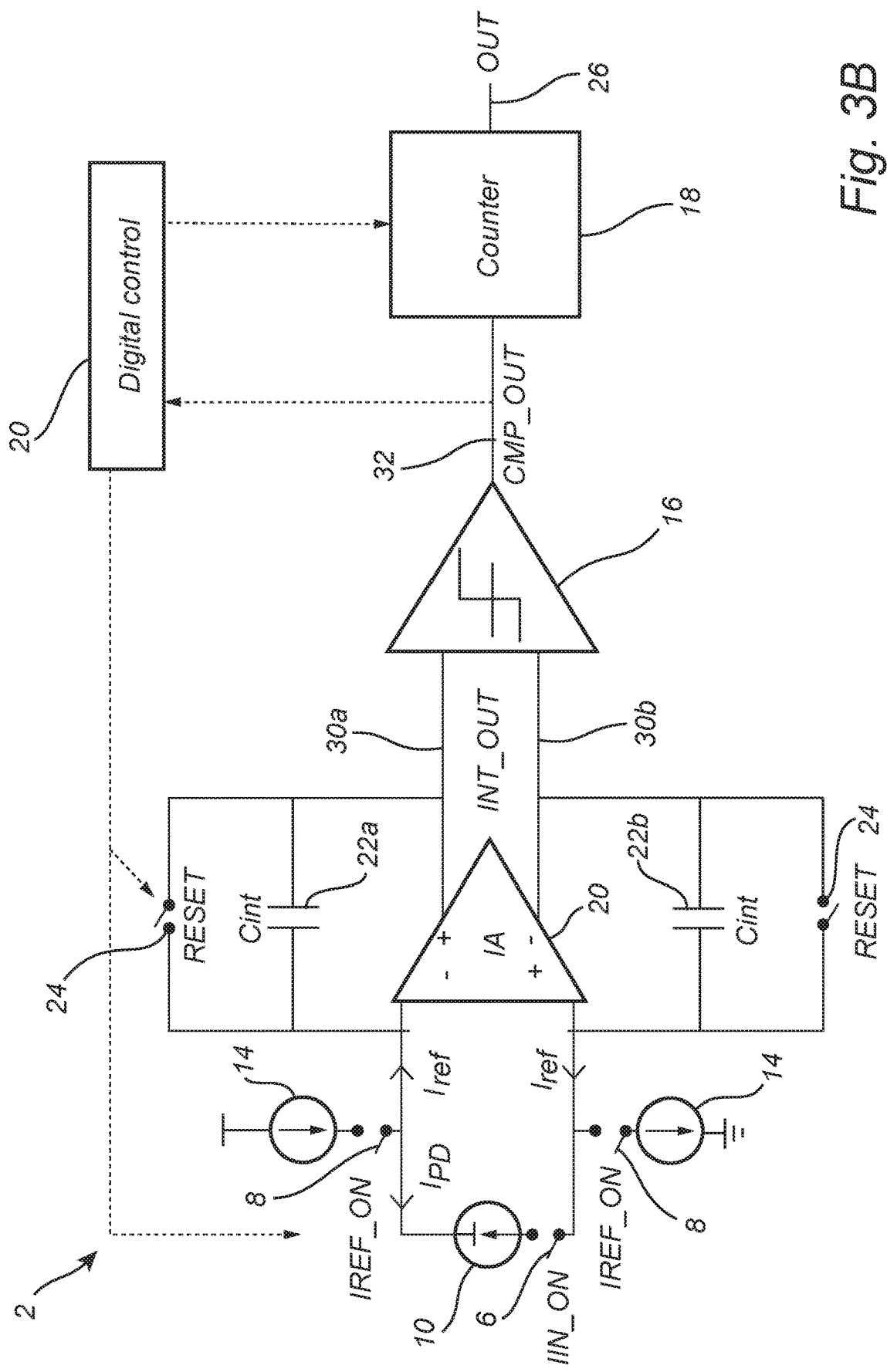
FIG. 3B shows a light-to-digital converter with a differential integrator with a pair of capacitors as feedback components.

FIG. 3B shows a different example light-to-digital converter 2. Here, the integrator 4 is a differential integrator with a pair of capacitors 22a, 22b as feedback components. The integrator 4 comprises an integrator amplifier 20 with a positive input, a negative input, and a differential output. The differential output comprises a positive output 30a and a negative output 30b, and constitutes a differential output out the integrator 4. A first capacitor 22a of the pair of capacitors is connected between the positive differential output 30a of the integrator amplifier 20 and the negative input of the integrator amplifier 20. A second capacitor 22b of the pair of capacitors is connected between the negative differential output 30b and the positive input of the integrator amplifier 20. The integrator 4 may be reset by closing two reset switches 24, connected in parallel, respectively, with the capacitor 22a and the capacitor 22b and controlled by the digital control unit 20. Two reference current generators 14 are connected, respectively, to the negative input and to the positive input of the integrator amplifier 20 through two respective switches 8. The light-to-current converter in the form of the photodiode 10 is connected between the negative input of the integrator amplifier 20 and the positive input of the integrator amplifier 20 through the switch 6.

Figure 3C:
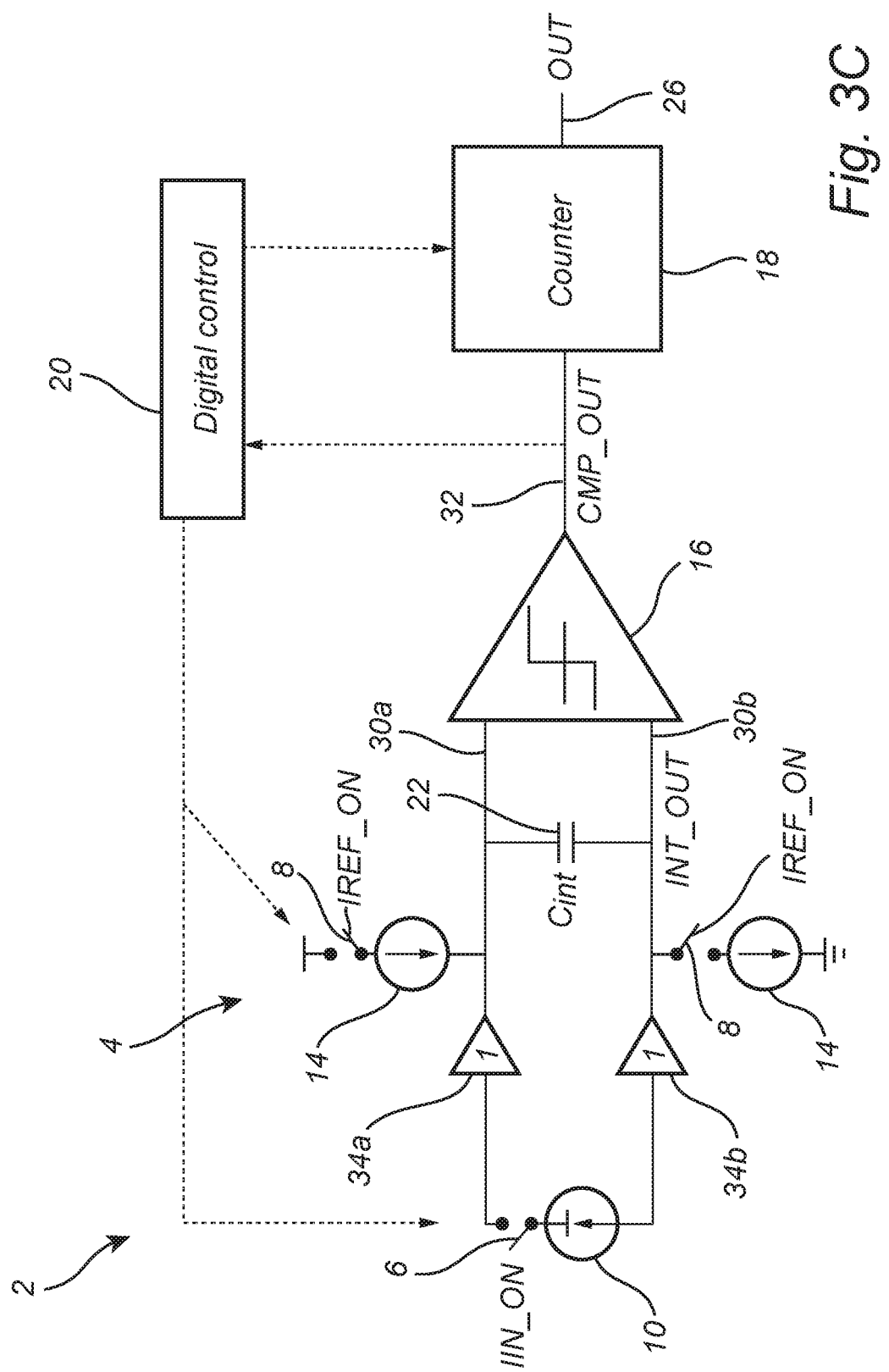
FIG. 3C shows a light-to-digital converter with an integrator based on current-sensing circuitry.

FIG. 3C shows yet another different example light-to-digital converter 2. Here, the integrator 4 is based on current-sensing circuitry and comprises a pair of current sensors 34a, 34b. The light-to-current converter, in the form of the photodiode 10, is connected between the input of the first current sensor 34a and the input of second current sensor 34b through the switch 6. Two reference current sources 14 are connected, respectively, at the output of the first current sensor 34a and at the output of the second current sensor 34b, through switches 8. An integrator capacitor $C_{int}$ 22 is connected between the output of the first current sensor 34a and at the output of the second current sensor 34b. The output of the first current sensor 34a and the output of the second current sensor 34b constitute a differential output of the integrator 4 and are both connected to respective inputs of the comparator 16.

Figure 4:
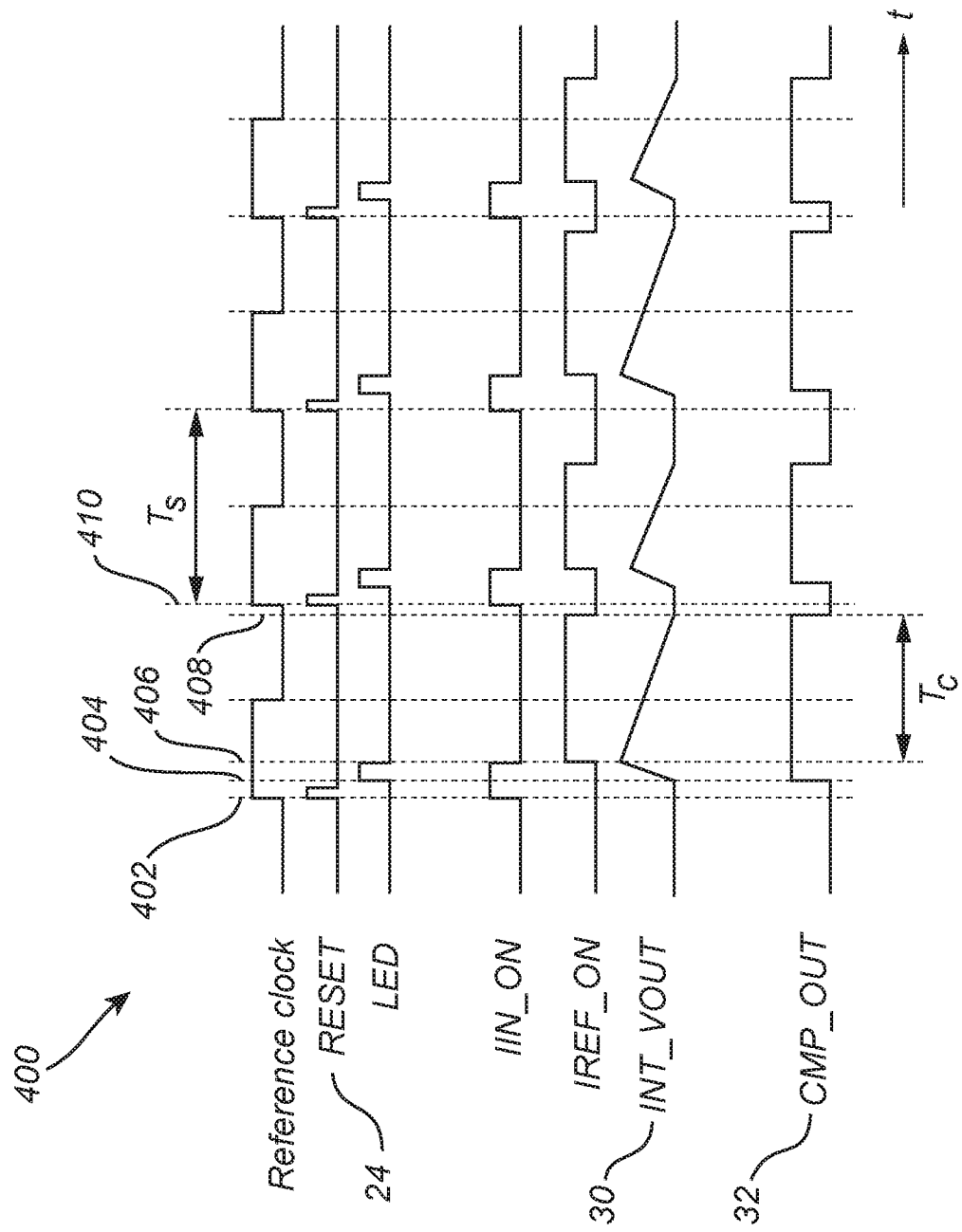
FIG. 4 shows a timing diagram.

FIG. 4 shows a timing diagram of signals during use of the light-to-digital converter 2 (cf. FIGS. 2, 3A, 3B, 3C), implementing a method of light-to-digital conversion 400.

Shown are signals for a reference clock, the reset line RESET 24, a control line for an LED 104, 204 (cf. FIGS. 1A, 1B), the control line IIN_ON for the switch 6 (cf. FIG. 2), the control line IREF_ON for the switch(es) 8 (cf. FIG. 2), the output 30 INT_VOUT of the integrator 4, and the output 32 CMP_OUT of the comparator 16.

The reference clock, setting the basic pacing of the method, may be generated internally in the digital control unit 20, or supplied to the digital control unit 20.

The reset line, the LED control line, the control line IIN_ON for the switch 6 for the light-to-current converter 10, and the control line IREF_ON for the switch or switches 8 for the reference current generator 14 or reference current generators 14 are controlled by the digital control unit 20 (cf. dashed lines in FIGS. 2, 3A, 3B, 3C), which controls the various stages of the light-to-digital conversion.

A typical procedure for light-to-digital conversion with the light-to-digital converter 2 (cf. FIGS. 2, 3A, 3B, 3C) will now be described.

At 402, typically on a leading edge of the reference clock, a pulse is sent on the reset line RESET by the digital control unit 20. This may shorten one or more switches 24 (cf. FIGS. 3A, 3B), resetting the integrator 4 to its baseline value, corresponding to zero integrated current.

Simultaneously, also at 402, the control line IIN_ON is put high by the digital control unit 20, resulting in the switch 6 connecting the light-to-current converter 10 to the current integrator 4. Meanwhile, the signal line IREF_ON is kept low by the digital control unit 20, meaning that the reference current source 14 is—or the reference current sources 14 are—disconnected from the current integrator 4.

Further, also at 402, the counter 18 is reset by the digital control unit 20 so that the counting by the counter 18 in the counting phase (see below) will start from zero. Alternatively, the counter may be reset at the start 406 of the counting phase, or at some point between 402 and the start 406 of the counting phase.

Thereafter, at 404, a light-collecting phase is started with the LED control line being put high by the digital control unit 20. The LED produces light, some of which is collected by the light-to-current converter 10. The current $I_{PD}$ (cf. FIG. 2) produced by the light-to-current converter 10 is integrated by the current integrator 4 (cf. FIG. 2), as is evident by the rising integrator output 30 INT_VOUT.

Thereafter, at 406, the light-collecting phase finishes with the LED control line being put low by the digital control unit 20. The light collecting phase, i.e., the time between 404 and 406, typically last between 1 μs and 200 μs.

Simultaneously, also at 406, the IIN_ON control line is put low by the digital control unit 20, making the switch 5 (cf. FIG. 2) disconnect the light-to-current converter 10 from the current integrator 4. The level of the integrator output 30 INT_VOUT now corresponds to the light collected by the light-to-current converter during the light-collecting phase. This value is now to be digitized.

For this purpose, still at 406, a counting phase is started. The IREF_ON control line is put high by the digital control unit 20, connecting the reference current source 14—or reference current sources 14—to the integrator 4 through the switch or switches 8. Since the reference current is connected as a negative integration input to the integrator 4, the integrator output 30 INT_VOUT starts falling.

Simultaneously, also at 406, the counter 18 is started by the digital control unit 20.

Eventually, at 408, the integrator output 30 INT_VOUT has dropped back to the baseline level. This is detected by the comparator 16. The output 32 CMP_OUT of the comparator 16 goes low, stopping the counter 18. Thus, the time $T_C$ is measured by the counter 18 and may be read out on the output line 28 OUT of the counter 18.

The time $T_C$ from start 406 to finish 408 of the counting phase corresponds to the value of the integrator output 30 INT_VOUT at the start of the counting phase at 406, in turn corresponding to the integrated current $I_{PD}$ during the light-collecting phase between 404 and 406, in turn corresponding to the light collected by the light-to-current converter 10 during the light-collecting phase. In the typical case of a constant current $I_{ref}$, the time $T_C$ is directly proportional to the to the value of the integrator output 30 INT_VOUT at the start of the counting phase at 406 and to the integrated current.

At 410, with a new leading edge of the reference clock, the method may be restarted as from 402. The procedure may alternate between using LEDs of different wavelengths, for example every other measurement being done with, respectively, a 730 nm LED and an 850 nm LED.

A typical value of the reciprocal of the reference clock period $1/T_s$ is 2-4 kHz.

A light-to-digital converter according to the present inventive concept was tested to achieve a 119 dB dynamic range with a power consumption of 74 μW (excluding LED power), compared to typically >200 μW for a light-to-digital converter using a transimpedance amplifier, an anti-aliasing filter, a sample/hold circuit, and an ADC separately.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A light-to-digital converter, comprising:
   a light-to-current converter;
   a current integrator with an integrator output resettable to a baseline value;
   and a counter with a digital output, wherein:
   said light-to-current converter is arranged to be connected as a positive integration input to said current integrator during a light-collecting phase, said current integrator integrating a current resulting from light-to-current conversion at said light-to-current converter, said integrator output starting from said baseline value and ending at a value to be digitized;
   a reference current source is arranged to be connected as a negative integration input to said current integrator during a counting phase subsequent to said light-collecting phase, integrating a reference current from said reference current source, said integrator output starting from said value to be digitized and ending at said baseline value, a time spent integrating said reference current corresponding to said value to be digitized; and
   said counter is configured for measuring said time and outputting a count corresponding to said value to be digitized.

2. The light-to-digital converter of claim 1, further comprising a comparator configured to compare said integrator output with a reference level corresponding to said baseline value, wherein an output of said comparator is connected to said counter.

3. The light-to-digital converter of claim 1, further comprising said reference current source.

4. The light-to-digital converter of claim 1, wherein said reference current is a constant current.

5. The light-to-digital converter of claim 1, wherein said light-to-current converter comprises a photodiode.

6. The light-to-digital converter of claim 1, wherein said light-to-current converter comprises a photomultiplier.

7. The light-to-digital converter of claim 1, wherein said current integrator is a single-ended integrator with a capacitor as a feedback component.

8. The light-to-digital converter of claim 1, wherein said current integrator is a differential integrator with a pair of capacitors as feedback components.

9. The light-to-digital converter of claim 1, wherein said current integrator is based on current-sensing circuitry.

10. A photoplethysmogram, PPG, system comprising the light-to-digital converter of claim 1.

11. A functional near-infrared spectroscopy, fNIRS, system comprising the light-to-digital converter of claim 1.

12. A method of light-to-digital conversion, comprising:
   during a light-collecting phase, a current integrator, having an integrator output, integrating a current resulting from light-to-current conversion at a light-to-current converter connected as a positive integration input, said integrator output starting from a baseline value and ending at a value to be digitized; and, thereafter,
   in a counting phase, said current integrator integrating a reference current connected as a negative integration input, said integrator output starting from said value to be digitized and ending at said baseline value, a time spent integrating said reference current corresponding to said value to be digitized, wherein a counter, providing a digital output, measures said time and outputs a count corresponding to said value to be digitized.

* * * * *